US00PP09051P

United States Patent [19]

Henny

[11] Patent Number: Plant 9,051

[45] Date of Patent: Jan. 31, 1995

[54] DIEFFENBACHIA NAMED 68814

[75] Inventor: Richard J. Henny, Tavares, Fla.

[73] Assignee: Florida Foundation Seed Producers, Inc., Greenwood, Fla.

[21] Appl. No.: 152,121

[22] Filed: Nov. 15, 1993

[51] Int. Cl.[6] ..... A01H 5/00

[52] U.S. Cl. ..... Plt./88.2

[58] Field of Search ..... Plt. 88.2

[56] References Cited

U.S. PATENT DOCUMENTS

P.P. 4504 2/1980 Welker ..... Plt. 88.2

P.P. 6420 11/1988 Stutzman ..... Plt. 88.2

*Primary Examiner*—James R. Feyrer

*Attorney, Agent, or Firm*—Robb & Robb; Frank B. Robb

[57] ABSTRACT

A Dieffenbachia cultivar having a unique leaf shape of long narrow configuration projecting from the main shoot in a star-like pattern, the leaves themselves having upper surface variegated coloration.

1 Drawing Sheet

This invention relates to Dieffenbachia plants and specifically to a new cultivar thereof which has some very unusual characteristics.

I have carried on an extensive program of breeding Dieffenbachia and as a result have produced several cultivars which are outstanding, the program being conducted in the vicinity of Apopka, Fla.

During the specific program, which resulted in the instant cultivar, many crosses and recrosses were resorted to and included some known and unknown species among them 'Lemon', 'Wilson's Delight', 'Perfection', and Lance, maculata lancifolia. As far as I am aware none of the plants used as part of the program is patented, nor do they closely resemble my new cultivar.

The traits which were observed as being consistently present have been repeatedly produced and determined to be basic characteristics of my new cultivar which is identified in the program as number 68814 and will be known in commerce as Diffenbachia 68814.

Asexual propagation has been caused by me near Tavares, Fla. and resulted from division tip cuttings and tissue culture to increase the number of plants used for evaluation, the traits found to be consistently produced in successive generations. The parent plants of this plant were denoted 68313 and 66508, and were proprietary material, but have since been destroyed to conserve greenhouse space.

Among the traits repeatedly observed and determined to be basic to provide the distinction in combination from other Dieffenbachia of the same general type such as D. 'Tropic Star' or any of those described by Bailey or Graf.

These include:

Unique leaf shape which consists of long narrow leaves projecting outward from the main shoot in a star-like pattern.

Leaf length averages approximately 4.5 times the width compared with most other Dieffenbachia cultivars have leaves that are twice as long as wide.

Attractive variegated foliage consisting of three colors on the upper leaf surface, with similar, yet slightly subdued, colorations on the lower leaf surface.

Leaves have dark green margins with areas of dark green, lighter green and almost-white blotches and spots distributed over the surface of the leaf.

Green-white petioles compliment the foliage to give the plant a brighter appearance.

Plants average 3 to 5 basal shoots which gives a full appearance beneath the main shoot.

An unusually short internode spacing causes specimens to be very compact and have a high density of leaves to plant height, even as specimens advance in age. This spacing seems to remain about the same even as the plants age, and is affected by light intensity.

Leaf petioles have long, wide wings of stipulate character, substantially only the tops of which are deep green, lobed and which wings extend nearly the entire length of the petioles; and are imbricated to an unusually high degree around the main stem of the plant, giving the plant the appearance of having a very wide, striated stem. Wing lobes are foliaceous.

Leaves are longer than wide to a much higher degree than normally seen in plants of this market class, and have unusually smooth margins that lack undulations to a marked degree of which have finer, less conspicuous leaf veining or ribs; the mibribs more nearly lacking green when compared to most similar plants in this market class.

The leaf coloration is further unusual in that the color patterns of the leaves do not follow the color pattern of the midrib and veins.

As stated heretofore, the plant remains substantially compact with advancing age and maturity and includes a higher canopy density than is normal due to the closely spaced internodes. This would suggest that there are probably longer periods possible between required transplants of specimens or reduced requirements for specimen renewal as plants grow too tall for their location. This is not a real problem since the plants do not grow to great heights.

The wings of this plant seem to be more distinctive, probably because they are formed on most of the length of the petioles and end in green foliaceous lobes.

To more particularly point out and assist in distinguishing my new cultivar the following distinctive characteristics are in part dependent on the color illustration herein provided with colors where referred to being measured against The Royal Horticultural Society Colour Chart.

In the drawing the plant is depicted in color as accurately as possible where photographic reproduction is resorted to and shows a mature plant which is six months old.

Classification: Dieffenbachia×c.v. 68814.

Propagation: Asexual production either by tissue culture or cuttings.

Plant: In a 15 cm standard pot after approximately 12 weeks of growth under appropriate conditions from a plantlet obtained by division, 68814 will be approximately 45-60 cm from the soil surface to the junction of the petioles of the most recently unfurled leaf, and approximately 50–65 in width. All measurements are based on the above parameters. The ultimate size of 68814, if planted in a sufficiently large container and grown under appropriate conditions, is widely variable.

Stem: The stem is erect in habit and will be approximately 20 mm in diameter at 30 mm above the soil surface. Internode distance will be approximately 15 mm at a height of 30 mm above the soil.

*Stem color.*—148B to 148C but is generally not visible due to the clasping nature of the petiole wings which surround the stem.

Petiole: The petiole color is 157A blending to 158A in some areas. The petiole (based on the third most recently expanded leaf) will be approximately 10 cm in length, with the clasping petiole wings extending from the point of attachment on the stem to within 2–20 mm the base of the leaf.

Leaf: The leaf will be lanceolate, with an acuminate apex and a cuneate to shortly attenuate base. The margin is entire. The lamina on either side of the midrib tends to be of slightly unequal widths, resulting in a slight curving of the blade towards the narrower side.

*Leaf dimensions.*—For the growing time and pot size indicated, the largest leaf will be approximately 9.5 cm×43 cm. An average leaf will be 7.5 cm×35 cm. The leaf thickness is medium.

Midrib: The midrib is thick and tapers toward the apex. It protrudes prominently from the abaxial side of the leaf.

Primary veins: The primary veins are sunken into the abaxial side and stand out from the abaxial side of the leaf blade. The color of the primary veins is the same as that of the adjacent leaf blade.

Color and pattern: The background color of the leaf is 1D to 150C with blotches of 145A and 147A irregularly paralleling the primary veins. The margins are 137A and this color varies in width from 1 mm to one half of the lamina. The abaxial surface of the mature leaf is essentially the same color as the abaxial surface except that the areas of color have less well defined edges and appeared fogged.

Axillary breaks: A plant will produce up to 5 lateral offshoots per main stem.

Blooming habit: Mature plants have been observed to flower in the spring in the greenhouse in Apopka, Fla.

Roots: Thick white roots with fine laterals.

I claim:

1. A new and distinct variety of Dieffenbachia plant, substantially as shown and described herein, characterized particularly as to novelty by its unique, long, narrow leaves projecting outwardly from the main shoot in a star-like pattern, its leaves being several times as long as wide, its variegated foliage of three colors on the upper leaf surface, the colors being dark green margins, areas of dark green, lighter green and almost white blotches and spots over the surface of the leaves, its green-white petioles, and its full appearance beneath the main shoot.

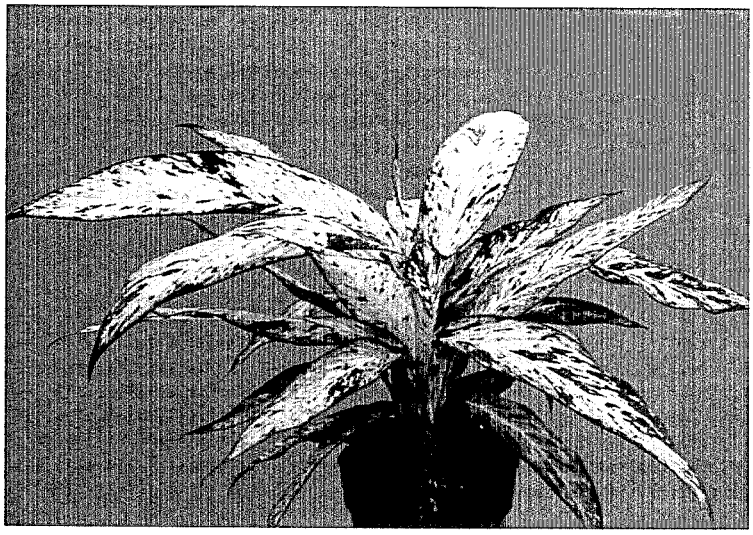

* * * * *